United States Patent
Nieminen et al.

(10) Patent No.: US 11,370,990 B2
(45) Date of Patent: Jun. 28, 2022

(54) PROCESS FOR ISOLATION OF STEROLS AND A FRACTION RICH IN FATTY ACIDS AND RESIN ACIDS

(71) Applicant: RAISIO NUTRITION LTD, Raisio (FI)

(72) Inventors: Ville Nieminen, Raisio (FI); Timo Suominen, Raisio (FI); Sami Kaatrasalo, Raisio (FI); Leena Koponen, Raisio (FI); Jari Ekblom, Raisio (FI)

(73) Assignee: RAISIO NUTRITION LTD, Raisio (FI)

( * ) Notice: Subject to any disclaimer, the term of this patent is extended or adjusted under 35 U.S.C. 154(b) by 0 days.

(21) Appl. No.: 17/056,023

(22) PCT Filed: Jun. 1, 2018

(86) PCT No.: PCT/EP2018/000284
§ 371 (c)(1),
(2) Date: Nov. 17, 2020

(87) PCT Pub. No.: WO2019/228602
PCT Pub. Date: Dec. 5, 2019

(65) Prior Publication Data
US 2021/0371772 A1    Dec. 2, 2021

(51) Int. Cl.
*C11B 13/00* (2006.01)
*C07J 9/00* (2006.01)
*C10L 1/02* (2006.01)

(52) U.S. Cl.
CPC .............. *C11B 13/005* (2013.01); *C07J 9/00* (2013.01); *C10L 1/026* (2013.01); *C10L 2200/0476* (2013.01)

(58) Field of Classification Search
CPC ..... C07J 9/00; C10L 1/026; C10L 2200/0476; C11B 13/005
See application file for complete search history.

(56) References Cited

U.S. PATENT DOCUMENTS

| 3,926,936 A | 12/1975 | Lehtinen |
| 2004/0024175 A1 | 2/2004 | Wong et al. |
| 2011/0034725 A1* | 2/2011 | Hamunen ................. C11C 1/10 562/400 |

FOREIGN PATENT DOCUMENTS

WO    WO-2008099051 A2    8/2008

OTHER PUBLICATIONS

Fernandes et al, "Phytosterols: Applications and Recovery Methods", Bioresource Technology, Elsevier, vol. 98, No. 12, (2007).
International Search Report and Written Opinion of the International Searching Authority, issued in PCT/EP2018/000284, dated Jan. 30, 2019; ISA/EP.

* cited by examiner

*Primary Examiner* — Ellen M McAvoy
*Assistant Examiner* — Chantel L Graham
(74) *Attorney, Agent, or Firm* — Harness, Dickey & Pierce, P.L.C.

(57) ABSTRACT

The invention relates to a process for recovering sterols and a fraction rich in fatty acids and resin acids from tall oil pitch, said process comprising a) saponifying the tall oil pitch with an alkali to hydrolyse esters included in the pitch to free alcohols and organic acids in salt form, b) acidulating the saponified pitch with a mineral acid to convert the organic acids in salt form into free organic acids and to form an organic phase and an aqueous phase; wherein mineral acid is provided in an amount to produce an aqueous phase with a pH value of at most 3.8, c) separating the aqueous phase with a pH value of at most 3.8 from the organic phase, d) evaporation fractionating the organic phase in a thin film evaporator to obtain a distillate rich in fatty acids and resin acids and a bottom fraction rich in sterols, e) evaporation fractionating the bottom fraction to obtain a distillate rich in sterols, and f) subjecting the sterols in the sterol-rich distillate to crystallisation purification, wherein the process excludes a step of adding alkali between step c) and step d).

20 Claims, No Drawings

PROCESS FOR ISOLATION OF STEROLS AND A FRACTION RICH IN FATTY ACIDS AND RESIN ACIDS

CROSS REFERENCE TO RELATED APPLICATIONS

This application is a 371 U.S. National Phase of International Application No. PCT/EP2018/000284, filed Jun. 1, 2018. The entire disclosure of the above application is incorporated herein by reference.

FIELD OF THE INVENTION

The present invention relates to a process for recovering sterols and a fraction rich in fatty acids and resin acids from tall oil pitch.

BACKGROUND OF THE INVENTION

Cardiovascular disease is counted among the most common diseases worldwide and its occurrence is further increasing. The most important individual risk factor is elevated serum LDL cholesterol level, and therefore, lowering of the blood concentrations of LDL cholesterol is the most effective single measure regarding both prevention and effective treatment of cardiovascular disease. Plant sterols e.g. sitosterol have since the early 1950's been known to reduce serum cholesterol levels. Food products enriched with plant sterols, or with their derivatives such as plant stanol ester, are widely available. In addition to food industry, plant sterols are also used in the pharmaceutical industry e.g. as raw materials for steroids and in the cosmetic industry as emulsifier. Plant sterols are commercially produced from vegetable oil deodorisation distillates and from wood based materials. Fatty acids and resin acids are widely used as raw-materials in the chemical industry, e.g. in soaps, detergents, lubricants, emulsifiers, rubber, paints, lacquers, inks and adhesives.

Crude tall oil is a major by-product of the pulping process, comprising mainly of fatty acids, resin acids and unsaponifiables, such as sterol compounds. When crude tall oil is distilled to tall oil, a distillation residue called tall oil pitch is formed. The composition of the tall oil pitch varies depending on the source of wood material and also on the pulping process used. Tall oil pitch comprises fatty acids, resin acids, sterol compounds, long-chain alcohols, terpene compounds and undefined degraded and/or polymerised molecules produced from these components as well as other wood extractive matter. The sterols and long-chain alcohols exist both in free form and as esters esterified with fatty acids. The majority of the sterols in tall oil pitch are in the fatty acid ester form, but there are also some free sterols present. The content of free sterols can for example be 1 w-% and the content of esterified sterols for example 12 w-% of the pitch, calculated as sterol equivalents i.e. expressed as free sterols. Tall oil pitch is usually burnt for producing energy or used in asphalt, but it can also be used as a source for recovering valuable components such as sterols, fatty acids and resin acids.

WO2008/099051 discloses two alternative processes for recovering fatty acids, resin acids and sterols from tall oil pitch. The first process option comprises saponifying the tall oil pitch, acidulating the saponified pitch, separating the aqueous phase from the organic phase, evaporation fractionating of the organic phase to obtain a distillate rich in sterols, fatty acids and resin acids and evaporation fractionating this distillate to obtain a bottom fraction rich in sterols and a distillate rich in fatty acids and resin acids, and subjecting the sterols in the sterol-rich bottom fraction to crystallisation purification. Acidulating the saponified pitch fastens the phase separation, but leads to a problem of increased re-esterification of the sterols with fatty acids and thus lower yields of sterols and fatty acids. The problem with re-esterification is solved by minimising the contact time between mineral acid, which functions as a catalyst for the re-esterification, and sterols and fatty acids by collecting both the fatty acids, resin acids and sterols in the first distillate and thereby eliminating the impact of the mineral acid catalyst. However, this kind of a distillation is very energy consuming and thus expensive.

The second process option disclosed in WO2008/099051 addresses the problem of re-esterification by treating the separated organic phase with alkali in order to destroy excess mineral acid used for acidulating the saponified pitch. Then in the first evaporation fractionation the alkali-treated organic phase is distilled to produce a distillate rich in fatty acids and resin acids and a bottom fraction rich in sterols. Then the sterol-rich bottom fraction is evaporation fractionated to obtain a distillate further enriched in sterols, and this sterol-rich distillate is finally subjected to crystallisation purification to obtain sterols.

However, there remains a need for an improved process to recover sterols as well as a fraction rich in fatty and resin acids from tall oil pitch.

BRIEF DESCRIPTION OF THE INVENTION

The present invention relates to a process for recovering sterols and a fraction rich in fatty acids and resin acids from tall oil pitch, said process comprising
 a) saponifying the tall oil pitch with an alkali to hydrolyse esters included in the pitch to free alcohols and organic acids in salt form,
 b) acidulating the saponified pitch with a mineral acid to convert the organic acids in salt form into free organic acids and to form an organic phase and an aqueous phase; wherein mineral acid is provided in an amount to produce an aqueous phase with a pH value of at most 3.8,
 c) separating the aqueous phase with a pH value of at most 3.8 from the organic phase,
 d) evaporation fractionating the organic phase in a thin film evaporator to obtain a distillate rich in fatty acids and resin acids and a bottom fraction rich in sterols,
 e) evaporation fractionating the bottom fraction to obtain a distillate rich in sterols, and
 f) subjecting the sterols in the sterol-rich distillate to crystallisation purification,
 wherein the process excludes a step of adding alkali between step c) and step d).

DETAILED DESCRIPTION OF THE INVENTION

It is thus an object of the present invention to provide a process for obtaining sterols from tall oil pitch. Also a fraction rich in fatty acids and resin acids is obtained. This can be utilised for further recovering fatty acids and resin acids or other valuable fractions of the acids. It can also be recirculated into a crude tall oil distillation process for distilling fatty acids and resin acids. In this way the sterols contained in this fraction can be re-circulated into the process for recovering. The process according to the invention is suitable for pine based tall oil pitch as well as for mixed tall oil pitch based on crude tall oil obtained from e.g. pine, spruce and/or birch. Pine pitch is the preferred starting material as the overall processing is smoother and the composition of unsaponifiables is such that it is easier to obtain sterol products that fulfil requirements of sterols to be used in foods and supplements. In addition pine pitch results in higher yields of sterols. However, the process also works well for mixed tall oil pitch.

It has now surprisingly been found that the prior addition of alkali to neutralise the mineral acid used to enhance the phase separation before performing the evaporation fractionations (option 2 in WO2008/099051) is unnecessary for avoiding re-esterification during the evaporation fractionations. It even seems to be beneficial to perform the corresponding process without this alkali addition.

Thus the present invention provides a process with faster overall throughput due to lacking the step of adding alkali. There is no need to estimate the amount of alkali needed to be added to the organic phase to neutralise the mineral acid as required in the closest prior known process. This estimation is time consuming and cumbersome because the water content of the organic phase also needs to be measured. As the overall separation process of sterols and a fraction rich in fatty acids and resin acids from tall oil pitch is faster a higher annual production using the process of the present invention can be accomplished with a simplified process lacking the equipment needed for the alkali addition.

The process according to the present invention thus omits one step of the prior known process and requires less investment as there is no need for equipment for alkali addition and subsequent mixing. Also the cost of laboratory analyses aiming at estimating the amount of alkali needed for neutralising the organic phase is eliminated. Further, the use of chemicals (alkali) is reduced and thus also less salts will be concentrated in the heavy residue.

An advantage of the present invention is further the simplified process in which the risk of formation of emulsion is eliminated. In the prior known process overloading of alkali may easily occur because of the challenging task to exactly estimate the amount of alkali needed and such overloading of alkali easily leads to a partial formation of an emulsion. Breaking such emulsion will add processing time and make the water removal (drying) more complicated. The emulsion formation would also impair the evaporation fractionation steps.

In this disclosure "plant sterols", "phytosterols", "sterols" and "sterol compounds" are used interchangeably. The sterols quantified in the analysis in this disclosure are sitosterol, campesterol, stigmasterol, sitostanol and campestanol. These are the most abundant sterols in tall oil pitch. The pitch however also contains other sterols. Sterols can be in a free form (sterol alcohol) or esterified to fatty acids (sterol fatty acid esters). For quantifying purposes, a term "sterol equivalent" is used. By the term "sterol equivalent" is meant sterols occurring in free and esterified forms, but their amount is expressed as the amount in free form. Thus, the amount of sterol equivalents corresponds to the total amount of sterols.

Thus the process according to the present invention comprises saponification of the tall oil pitch. This saponification step a) is performed with alkali to hydrolyse the esters in the tall oil pitch to free alcohols (sterols and long-chain alcohols) and organic acids (fatty and resin acids) in salt form. The alkali used is preferably an aqueous solution of an alkali metal hydroxide. Preferably sodium hydroxide or potassium hydroxide or a combination thereof is used. For example, a water solution of 20 w-% sodium hydroxide can be used. Preferably water is added to a level of at least 10 w-%, preferably to the level of 10-100 w-%, more preferably to the level of 15-60 w-% and most preferably to the level of at least 30 w-% of the amount of tall oil pitch. This amount of water includes also the water in which the added alkali is dissolved in. Thus in the saponification step there is present at least 10 w-%, preferably 10 to 100 w-%, more preferably 15-60 w-% and most preferably 20 to 55 w-% water of the amount of tall oil pitch. In the saponification step sterol esters are converted to free sterols and fatty acids in salt form. The amount of alkali metal hydroxide is preferably sufficient to provide substantially complete saponification of sterol esters in the pitch to free sterols and fatty acids. The amount of alkali metal hydroxide should be at least equal the amount defined by the saponification number of the pitch. Preferably the alkali is added in an excess of e.g. 1-15% or more preferably in an excess of about 7-13%. Typically the saponification is performed at a temperature of 80-220° C., preferably 90-200° C., more preferably 95-180° C. and most preferably 100-160° C. The saponification is preferably performed at a temperature of at most 160° C., more preferably at most 150° C., still more preferably at most 140° C. and most preferably less than 130° C. It is possible to use an organic co-solvent, such as ethanol, propanol, hexane, heptane or ketones e.g. methyl ethyl ketone, or mixtures thereof. However, preferably a co-solvent is not used, as it makes the saponification step more complicated and more expensive, and the co-solvent needs to be recovered before the subsequent process steps. In order to enable overall good yields of resin and fatty acids and sterols in the process according to the present invention it is important that the saponification is efficient. Thus the saponification is performed to provide an amount of free sterol of at least 90 w-%, preferably at least 95 w-% and most preferably at least 98 w-% of the sterol equivalents in the tall oil pitch.

The acidulation step b) of the saponified tall oil pitch is performed with a mineral acid, such as sulphuric acid or hydrochloric acid, and preferably sulphuric acid is used. Typically an aqueous solution of 30 w-% sulphuric acid can be used, but also other concentrations may be used e.g. 10 to 93 w-%. The amount of mineral acid is such that the pH of the aqueous phase is at most 3.8, preferably at most 3.4, more preferably at most 3.0. Preferably the pH is at least 1.0, more preferably at least 1.3 and most preferably at least 1.4. Thus a pH of typically 1.0-3.0 is very preferred and 1.3-3.0 most preferred. After the acidulation, the temperature of the reaction mixture is maintained below 100° C. e.g. for 5-120 minutes without stirring, to allow the aqueous and the organic phases to separate.

Preferably the acidulation step b) is performed to a saponified pitch having at least 90 w-%, preferably at least 95 w-% and most preferably at least 98 w-% of the sterol equivalents present as free sterols. This improves the efficiency of the overall process.

The acidulation improves the phase separation step c) by making it faster and more efficient. Preferably the phase separation is accomplished by allowing the acidulated saponified tall oil pitch to stand and settle for at most 120 minutes, more preferably at most 90 minutes, still more preferably at most 60 minutes, even more preferably at most 30 minutes and most preferably at most 15 minutes. The residual water content of the organic phase after the phase separation is typically at most 5 w-%, preferably at most 4 w-%, more preferably at most 3.5 w-%.

The residual water can be removed from the organic phase e.g. by a vacuum degasser to produce a dried organic phase.

The phase separation is effective enough to be accomplished only by allowing the acidulated and saponified pitch to stand for a short time e.g. 5-120 min and to leave just a low level of residual water in the organic phase. Preferably the organic phase is subjected to a pretreatment step for removing residual water from the organic phase prior to step d), preferably carried out in a vacuum degasser. Drying of the organic phase is most preferably realised as a first step in the evaporation fractionation by a vacuum degasser.

By "organic phase" is in this disclosure meant the organic phase containing the residual amount of water, i.e. the matter that is fed into the drying step i.e. into the evaporation units.

The evaporation fractionating steps d) and e) according to the present invention are preferably performed by feeding the bottom fraction of the first evaporator continuously into the second evaporator.

In the first evaporation fractionating step d) the fatty acids and resin acids are distilled. This evaporation fractionation can be performed by using a thin film evaporator with no partial condenser, i.e. the thin film evaporator is not equipped with a partial condenser. In this equipment the distillate obtained from the thin film evaporator is not fed to a partial condenser. Thus the fraction or part of the fraction rich in fatty acids and resin acids is preferably not recirculated into the thin film evaporator.

Alternatively and preferably, the thin film evaporator is a wiped film evaporator (WFE).

The wiped film evaporator operates at a temperature in the range of preferably 160° C. to 250° C., more preferably 180° C. to 240° C. and at a pressure in the range of preferably 10 to 1000 Pa, more preferably 50 to 500 Pa.

The distillate rich in fatty acids and resin acids obtained in the first thin film evaporation (here also called a fraction rich in fatty acids and resin acids) can be subjected to further distillation to obtain separately fatty acids and resin acids or valuable fractions of these organic acids.

It has now been realised that the distillate rich in fatty acids and resin acids from step d) preferably can be recirculated into a crude tall oil distillation process for distilling fatty acids and resin acids and leaving tall oil pitch as bottom fraction. This is a convenient way of making use of the fatty and resin acids included in the distillate fraction rich in fatty acids and resin acids obtained in the process step d) of the present invention. At the same time also the sterols contained in the distillate of step d) can be recirculated into the process of the invention by using the resulting tall oil pitch as starting material or as part of the starting material in the process of the invention. In this way the overall recovery of sterols from the pitch is more efficient.

Preferably the fraction rich in fatty acids and rosin acids can be used for the preparation of biodiesel.

The bottom fraction rich in sterols obtained in step d) is introduced to a second evaporation fractionating step e). The second evaporation fractionation is preferably performed in a thin film evaporator to distil sterols and to leave heavy components in the bottom fraction. The second thin film evaporator is preferably a short path evaporator (SPE). The short path evaporator operates preferably at a temperature in the range of 220° C. to 280° C., more preferably 230° C. to 270° C. and at a pressure of 1 to 100 Pa, more preferably 5 to 50 Pa.

It has been realised that in order to obtain a high sterol concentration in the sterol-rich distillate obtained in the second distillation a quite high amount of distillate is to be produced in the second evaporation fractionation. Thus the evaporation fractionation step d) is performed to produce an amount of distillate of at least 10 w-%, preferably at least 15 w-%, more preferably at least 20 w-% and most preferably at least 25 w-% of the amount of organic phase obtained in step c).

It was also surprisingly noticed the most preferred way of performing steps d) and e) in the process of the present invention is to use a wiped film evaporator in step d) and a short path evaporator in step e). The removal of the residual water from the organic phase is then preferably realised by a vacuum degasser preceding the wiped film evaporator.

After the evaporation fractionating, the sterols in the distillate are subjected to purification by using conventional crystallisation processes (step f) of the present process), such as solvent crystallisation to obtain a sterol blend mainly consisting of 4-desmethyl sterols and limited amounts of other sterol compounds. Preferably the obtained sterol product shall fulfil the regulatory requirements set on pine/wood based sterol blends by main jurisdictions, such as in the EU. Preferably the solvent comprises hydrocarbon, alcohol and optionally water. More preferably the solvent comprises methyl ethyl ketone, methanol and water. The crystallisation purification is preferably performed using two crystallisations. One or two washing steps may also be included in the purification. The crystallisation purification can be performed according to any prior known methods.

The process according to the present invention is surprisingly well suited for using mixed tall oil pitch as starting material.

One additional benefit with this method is that the sterols preferably are more efficiently concentrated in the sterol-rich distillate than for corresponding fractions obtained from acidulated/neutralised saponified pitch in prior known processes. A high sterol content of the fraction subjected to sterol crystallisation is of great value because an improved sterol yield can thereby be obtained. The sterol content of tall oil pitch originating from pine based pulp is usually already higher than in pitches from mixed pulp. Thus, when applying this process to pine pitch a higher content of sterols would be obtained in the sterol-rich fraction in comparison to what is shown in the current Example.

In this description the amounts given in percentages mean percentage by weight (w-%) unless otherwise is stated. The sterols quantified in the analysis in this disclosure are sitosterol, campesterol, stigmasterol, sitostanol and campestanol. The analysis was performed by gas chromatography.

The invention will be described in greater detail by means of the following non-limiting examples.

EXAMPLE 1

2.0 kg of tall oil pitch originating from mixed pine and birch based pulp (containing 13.8 w-% sterol equivalents) was heated to 85° C. in an autoclave and 1.0 kg of 20% NaOH was added. The reaction mixture was heated to increase the temperature from 85° C. to 140° C. during 40 minutes. This temperature was kept for 30 minutes and then the mixture was cooled to 95° C. during 50 minutes. The saponification was performed with continuous mixing. The saponification was almost complete because the amount of free sterols was measured to 13.6 w-%, corresponding to 99% of the sterol equivalents contained in the starting pitch. 895 g of 30% sulphuric acid was added to the saponified tall oil pitch and the mixture was further mixed for 60 minutes after which the mixing was stopped for 60 minutes to allow the water phase and organic phase to separate. The water phase (with a pH of 1.6) was discharged and 1933 g of organic phase was collected. The temperature remained at about 95° C. during the acidulation and phase separation.

Then the evaporation fractionation was performed using the following arrangement in a continuous way. The organic phase was distilled in a wiped film evaporator (WFE) at 210° C. and 100 Pa and the bottom fraction from the WFE was distilled in a short path evaporator (SPE) at 240° C. and 10 Pa. The fractions were collected during the time the system worked under stable conditions (discharging fractions at the start and end of the distillation). Thus, water and lights end (small amount of low-boiling organic compounds) was collected in the cold trap in an amount of 5.2 w-% of the total amount of collected fractions. The WFE distillate fraction was 26.1 w-% of the total amount of collected fractions and it corresponds to the fraction rich in fatty and resin acids. This distillate fraction contained 2.8 w-% sterols. The sterol-rich residue was distilled in the SPE to obtain 43.3 w-% of the total amount of collected fractions of a sterol-rich distillate containing 28.5 w-% sterols. The bottom fraction (the residue) from the SPE distillation (25.4 w-% of the total amount of collected fractions) contained 1.6 w-% sterols (1.5 w-% were esterified). Based on the sterol amount from the fractions the sterol yield in the sterol-rich SPE distillate fraction was calculated to be 91.6 w-%.

EXAMPLE 2: COMPARISON TEST WITH ALKALI ADDITION TO THE ORGANIC PHASE BEFORE THE THIN FILM EVAPORATION

The reaction was carried out as described in Example 1, except that after discharging the water phase the water content of the organic phase (4.2 wt-%) was determined and the pH (1.6) of the water phase was measured in order to determine the amount of NaOH to be added to neutralize remaining sulfuric acid present in the organic phase. This took 90 minutes. Then 200 µl of 50% NaOH was added to the organic phase (produced as disclosed in Example 1) and the reaction mixture was mixed for 60 minutes at 95° C. The evaporation fractionation apparatus and conditions were kept the same as in Example 1. The WFE distillate fraction was 23.8 w-% of the total amount of collected fractions and 4.1 w-% of the total amount of collected fractions was collected in the cold trap. The sterol-rich residue from the WFE was distilled in the short path evaporator (SPE) to obtain 45.8 w-% sterol-rich distillate of the total amount of collected fractions. The sterol-rich distillate contained 28.0 w-% sterols. The bottom fraction (26.3 w-% of the total amount of collected fractions) contained 2.1 w-% sterols (1.9 w-% were esterified). Based on the sterol amount from the fractions the sterol yield the sterol-rich distillate was calculated to be 90.6 w-%.

EXAMPLE 3: CRYSTALLISATION PURIFICATION OF THE STEROLS OBTAINED IN EXAMPLE 1

167 g of the SPE distillate produced in Example 1 was dissolved by refluxing in 176 g of a solvent mixture, which contained 5% water, 38% methanol and 57% of methyl ethyl ketone. After dissolution sterols were crystallized by cooling to 30° C. and kept at 30° C. overnight. The crystals were filtrated by a pressure filter and washed at 25° C. with a solvent mixture of the same composition as used in the crystallisation. The sterol crystals were dried and analysed. The yield of sterol crystals was 72 w-% and the product contained 95 w-% of sitosterol, campesterol, stigmasterol, sitostanol and campestanol. By applying a second recrystallisation step a sterol product with even higher sterol content can be obtained.

Evaluation of Results from Example 1 and 2

Example 1 is a process according to the current invention and Example 2 is the corresponding process but with the addition of alkali to neutralise the excess mineral acid which was added in the acidulation step to enhance the phase separation. As can be seen in Table 1 from the sterol contents of the fractions, sterol esters could only be found in the SPE residues of Examples 1 (1.5 w-% equivalents)

TABLE 1

Comparison of features and results of Examples 1 and 2

| | Example 1 | Example 2 |
|---|---|---|
| Process conditions | | |
| Feed rate (g/h) | 440 | 440 |
| WFE temperature (° C.) | 210 | 210 |
| WFE pressure (Pa) | 100 | 100 |
| SPE temperature (° C.) | 240 | 240 |
| SPE pressure (Pa) | 10 | 10 |
| Collected fractions in w-% | | |
| Cold trap/Degassing | 5.2 | 4.1 |
| WFE distillate | 26.1 | 23.8 |
| SPE distillate | 43.3 | 45.8 |
| SPE residue | 25.4 | 26.3 |
| Sterol content (w-%) of the fractions: sterol equivalents/free sterols/esterified sterols | | |
| Cold trap | 0/0/0 | 0/0/0 |
| WFE distillate | 2.8/2.8/0 | 3.3/3.3/0 |
| SPE distillate | 28.5/28.5/0 | 28.0/28.0/0 |
| SPE residue | 1.6/0.1/1.5 | 2.1/0.2/1.9 |
| Calculated results | | |
| Sterol yield * (w-%) | 91.6 | 90.6 |
| Amount of esterified sterols (w-%) ** | 0.38 | 0.50 |

* Sterols contained in the sterol-rich fraction (SPE distillate) of the total sterol content in all fractions, given as w-%
** Amount of sterol equivalents that are present as esters calculated on the total weight of the fractions and 2 (1.9 w-% equivalents). At the last line of Table 1 the amount of esterified sterols (amount of sterol equivalents that are present as esters) is calculated on the total weight of the fractions. In Example 2 a higher amount of sterol ester is present. Thus, despite the addition of alkali which was aimed to reduce the re-esterification of sterols more sterol ester was formed during the process of Example 2.

The smaller amount of water and low-boiling organic compounds obtained in the cold trap in Example 2 might indicate some emulsification has occurred and thus more water remained in the organic phase. It may also relate to the higher amount of sterol esters formed in Example 2.

The sterol yield in the evaporations is slightly better in Example 1. The same applies for the sterol content in the SPE distillate in Example 1. This means that the process according to the present invention gives improved results. However, the main benefit is the simplification of the process by omitting the alkali addition and the problems related to that.

The invention claimed is:

1. A process for recovering sterols and a fraction rich in fatty acids and resin acids from tall oil pitch, said process comprising
    a) saponifying the tall oil pitch with an alkali to hydrolyse esters included in the pitch to free alcohols and organic acids in salt form,
    b) acidulating the saponified pitch with a mineral acid to convert the organic acids in salt form into free organic acids and to form an organic phase and an aqueous phase; wherein mineral acid is provided in an amount to produce an aqueous phase with a pH value of at most 3.8, c) separating the aqueous phase with a pH value of at most 3.8 from the organic phase, d) evaporation fractionating the organic phase in a thin film evaporator to obtain a distillate rich in fatty acids and resin acids and a bottom fraction rich in sterols, e) evaporation fractionating the bottom fraction to obtain a distillate rich in sterols, and f) subjecting the sterols in the sterol-rich distillate to crystallisation purification, wherein the process excludes a step of adding alkali between step c) and step d).

2. The process according to claim 1, wherein the mineral acid is provided in the acidulation in an amount to produce an aqueous phase with a pH value of at most 3.4.

3. The process according to claim 1, wherein the sterols in the sterol-rich distillate are subjected to purification by solvent crystallisation, wherein the solvent comprises hydrocarbon, alcohol and optionally water.

4. The process according to claim 1, wherein the organic phase prior to step d) is subjected to a pretreatment step for removing water from the organic phase, preferably carried out in a vacuum degasser.

5. The process according to claim 1, wherein the thin film evaporator in step d) is a wiped film evaporator.

6. The process according to claim 1, wherein the thin film evaporator in step d) is not being equipped with a partial condenser.

7. The process according to claim 5, wherein the wiped film evaporator operates at a temperature in the range of 160° C. to 250° C. and at a pressure in the range of 10 to 1000 Pa.

8. The process according to claim 1, wherein the evaporation fractionation step d) produces an amount of distillate of at least 10 w-%, of the amount of organic phase obtained in step c).

9. The process according to claim 1, wherein the evaporation fractionation of step e) is carried out in a short path evaporator.

10. The process according to claim 9, wherein the short path evaporator operates at a temperature in the range of 220° C. to 280° C. and at a pressure of 1 to 100 Pa.

11. The process according to claim 1, wherein the saponification step a) is performed in the presence of NaOH and/or KOH and at least 10 w-%, water calculated on the weight of the tall oil pitch.

12. The process according to claim 1, wherein the amount of free sterol after the saponification step a) is at least 90 w % of the sterol equivalents.

13. The process according to claim 1, wherein the tall oil pitch is mixed tall oil pitch.

14. The process according to claim 1, wherein the distillate rich in fatty acids and resin acids from step d) is recirculated into a crude tall oil distillation process for distilling fatty acids and resin acids and leaving tall oil pitch as bottom fraction.

15. The process according to claim 1, wherein the distillate rich in fatty acids and resin acids from step d) is utilised in the preparation of biodiesel.

16. The process according to claim 1, wherein the mineral acid is provided in the acidulation in an amount to produce an aqueous phase with a pH value of 1.0-3.0.

17. The process according to claim 5, wherein the wiped film evaporator operates at a temperature in the range of 180° C. to 240° C. and at a pressure in the range of 50 to 500 Pa.

18. The process according to claim 1, wherein the evaporation fractionation step d) produces an amount of distillate of at least 20 w-% of the amount of organic phase obtained in step c).

19. The process according to claim 1, wherein the saponification step a) is performed in the presence of NaOH and/or KOH and 20-55 w-% water calculated on the weight of the tall oil pitch.

20. The process according to claim 1, wherein the amount of free sterol after the saponification step a) is at least 98 w-% of the sterol equivalents.

* * * * *